(12) United States Patent
Murphy

(10) Patent No.: US 7,105,028 B2
(45) Date of Patent: Sep. 12, 2006

(54) TISSUE PRESERVING AND MINIMALLY INVASIVE HIP REPLACEMENT SURGICAL PROCEDURE

(75) Inventor: Stephen B. Murphy, Medford, MA (US)

(73) Assignee: Wright Medical Technology, Inc., Arlington, TN (US)

( * ) Notice: Subject to any disclaimer, the term of this patent is extended or adjusted under 35 U.S.C. 154(b) by 240 days.

(21) Appl. No.: 10/691,800

(22) Filed: Oct. 21, 2003

(65) Prior Publication Data

US 2005/0081867 A1 Apr. 21, 2005

(51) Int. Cl.
*A61F 2/32* (2006.01)
*A61B 17/16* (2006.01)

(52) U.S. Cl. .................. 623/22.4; 623/22.11; 606/80

(58) Field of Classification Search ............. 623/22.11, 623/22.4; 128/898; 606/80
See application file for complete search history.

(56) References Cited

U.S. PATENT DOCUMENTS

| | | | |
|---|---|---|---|
| 3,685,058 A | 8/1972 | Tronzo | |
| 3,859,992 A | 1/1975 | Amstutz | |
| 3,874,003 A | 4/1975 | Moser et al. | |
| 4,305,394 A | 12/1981 | Bertuch, Jr. | |
| 4,399,813 A | 8/1983 | Barber | |
| 4,475,549 A | 10/1984 | Oh | |
| 4,528,980 A | 7/1985 | Kenna | |
| 4,632,111 A | 12/1986 | Roche | |
| 4,662,891 A | 5/1987 | Noiles | |
| 4,677,972 A | 7/1987 | Tornier | |
| 4,716,894 A | 1/1988 | Lazzeri et al. | |
| 4,878,918 A | 11/1989 | Tari et al. | |
| 4,994,064 A | 2/1991 | Aboczsky | |
| 5,030,221 A | 7/1991 | Buechel et al. | |
| 5,037,424 A | 8/1991 | Aboczsky | |
| 5,061,270 A | 10/1991 | Aboczsky | |
| 5,098,437 A | 3/1992 | Kashuba et al. | |
| 5,108,448 A | 4/1992 | Gautier | |
| 5,108,452 A | 4/1992 | Fallin | |
| 5,116,339 A | 5/1992 | Glock | |
| D331,461 S | 12/1992 | Lester | |
| 5,167,399 A | 12/1992 | Delomel | |
| 5,171,243 A | 12/1992 | Kashuba et al. | |
| 5,171,313 A | 12/1992 | Salyer | |
| 5,190,422 A | 3/1993 | Lechot | |
| 5,217,499 A | 6/1993 | Shelley | |
| 5,250,051 A | 10/1993 | Maryan | |
| 5,261,915 A | 11/1993 | Durlacher et al. | |
| 5,284,483 A | 2/1994 | Johnson et al. | |
| 5,320,625 A | 6/1994 | Bertin | |
| 5,344,461 A | 9/1994 | Philpot | |
| 5,364,403 A | 11/1994 | Petersent et al. | |

(Continued)

FOREIGN PATENT DOCUMENTS

EP 0147339 A2 7/1985

(Continued)

OTHER PUBLICATIONS

Murphy, Minimally Invasive Hip Surgery, From www.stephensmurphy.com (2003).

(Continued)

*Primary Examiner*—Corrine McDermott
*Assistant Examiner*—Thomas J. Sweet

(57) ABSTRACT

A minimally invasive hip replacement surgical procedure that is also tissue preserving is disclosed. By making a superior incision, rather than a posterior incision, neither the posterior hip capsule, nor the gluteus medius or minimus are dissected. This results in improved post-operative results in the form of less dislocations and better healing.

18 Claims, 11 Drawing Sheets

U.S. PATENT DOCUMENTS

| | | | |
|---|---|---|---|
| 5,417,696 A | 5/1995 | Kashuba | |
| 5,458,637 A | 10/1995 | Hayes | |
| 5,474,560 A | 12/1995 | Rohr, Jr. | |
| 5,486,181 A | 1/1996 | Cohen et al. | |
| 5,499,985 A | 3/1996 | Hein et al. | |
| 5,507,748 A | 4/1996 | Sheehan et al. | |
| 5,658,290 A | 8/1997 | Lechot | |
| 5,683,399 A | 11/1997 | Jones | |
| 5,904,688 A | 5/1999 | Gilbert | |
| 5,928,287 A | 7/1999 | Keller | |
| 5,968,049 A | 10/1999 | DaRold | |
| 6,063,123 A | 5/2000 | Burrows et al. | |
| 6,063,124 A | 5/2000 | Amstutz | |
| 6,106,536 A | 8/2000 | Lechot | |
| 6,110,211 A * | 8/2000 | Weiss | 623/23.11 |
| 6,129,732 A | 10/2000 | Lechot | |
| 6,132,469 A | 10/2000 | Schroeder | |
| 6,264,647 B1 | 7/2001 | Lechot | |
| 6,482,209 B1 | 11/2002 | Engh et al. | |
| 6,626,913 B1 | 9/2003 | McKinnon et al. | |
| 6,676,706 B1 * | 1/2004 | Mears et al. | 623/22.4 |
| 6,860,903 B1 * | 3/2005 | Mears et al. | 623/22.11 |
| 2001/0006593 A1 | 7/2001 | Lechot | |
| 2002/0002365 A1 | 1/2002 | Lechot | |
| 2002/0010470 A1 | 1/2002 | Lechot | |
| 2002/0099447 A1 | 7/2002 | Mears et al. | |
| 2002/0116067 A1 | 8/2002 | Mears et al. | |
| 2002/0193797 A1 | 12/2002 | Johnson et al. | |
| 2003/0004513 A1 | 1/2003 | Guzman et al. | |
| 2003/0050645 A1 | 3/2003 | Parker et al. | |
| 2003/0097135 A1 | 5/2003 | Penenberg | |
| 2003/0158559 A1 | 8/2003 | Diaz | |
| 2003/0181916 A1 | 9/2003 | Wolford | |
| 2003/0220696 A1 | 11/2003 | Mears et al. | |
| 2003/0220698 A1 * | 11/2003 | Mears et al. | 623/22.4 |
| 2003/0229352 A1 | 12/2003 | Penenberg | |
| 2003/0229356 A1 | 12/2003 | Dye | |
| 2003/0229357 A1 | 12/2003 | Dye | |
| 2005/0096748 A1 * | 5/2005 | Yoon | 623/22.4 |

FOREIGN PATENT DOCUMENTS

| | | |
|---|---|---|
| EP | 0357270 A1 | 3/1990 |
| EP | 0470912 A2 | 2/1992 |
| EP | 1149562 A2 | 10/2002 |
| EP | 1149562 A3 | 1/2003 |
| GB | 2372707 A | 9/2002 |
| WO | WO03/057049 A1 | 7/2003 |
| WO | WO03/065906 A2 | 8/2003 |

OTHER PUBLICATIONS

Author unknown. Short External Rotator Muscles of the Hip. From www.biyee.net/running/injury/short_rotators.html (2002).

Precimed tool advertisement (2002).

Minimally Invasive Hip Surgery and Future Developments, From www.essexhipsurgeon.co.uk/minimally_invasive_hip_replacement_surgery.html (2003).

Innomend MIS catalog (2003.

McTighe, A New Era of Minimally Invasive Surgical Approaches for THA, Joint Implant Surgery & Research Foundation Update (Dec., 2002).

Berry, et al. Symposium on Minimally Invasive THA, J. Bone Joint Surg. 85A: 2235-2246 (2003).

Pellegrini, et al., Surgical Approaches to the Hip Joint. In: Surgery of the Musculoskeletal System (C. M. Evarts, Ed.), Churchill Livingstone (New York, NY) Chapter 94, pp. 2735-2756 (1990).

* cited by examiner

TISSUE PRESERVING AND MINIMALLY INVASIVE HIP REPLACEMENT SURGICAL PROCEDURE

RELATED APPLICATIONS

This application is related to assignee's U.S. patent application Ser. No. 10/691,143, filed Oct. 21, 2003.

FIELD OF THE INVENTION

This invention is generally related to total hip arthroplasty. The invention is specifically related to a hip replacement surgical procedure that is both minimally invasive and tissue preserving.

BACKGROUND OF THE INVENTION

The move towards minimally invasive surgical ("MIS") procedures for hip arthroplasty has begun and continues. To date, some of the proposed MIS procedures incorporate some similarities to the traditional open procedures. For example, posterior incisions and approaches may be used, the hip may still be dislocated during the bulk of femoral and acetabular preparation, the short external rotators may be dissected, or the gluteal muscles and in particular the gluteus medius and minimus may be dissected. In other words, the MIS methods still result in the dissection and disruption of important soft tissue; even if in an amount less than in conventional open techniques.

These similarities with traditional open methods resulted in MIS procedures that have similar post-operative results as open-methods, e.g., longer recovery times and increased dislocations. Thus, the only real benefit obtained by using these MIS techniques was the smaller incision. Accordingly, there is room for improvement within the art.

SUMMARY OF THE INVENTION

It is an object of the invention to provide an improved MIS hip replacement surgical procedure.

It is an object of the invention to provide an improved MIS hip replacement surgical procedure that provides for more post-operative benefits than just a decreased incision size.

It is an object of the invention to provide an improved MIS hip replacement surgical procedure that preserves rather than dissects soft tissue.

It is an object of the invention to provide an improved MIS hip replacement surgical procedure that provides for minimized aggravation of soft tissue during the procedure.

These and other objects of the invention are achieved by a tissue preserving surgical procedure for the replacement of a hip joint, including the step of making a superior incision for accessing the hip joint.

These and other objects of the invention are also achieved by a minimally invasive surgical procedure for the replacement of a hip joint, including the step of making a superior capsulotomy for accessing the hip joint.

These and other objects of the invention are also achieved by a minimally invasive and tissue preserving surgical procedure for the replacement of a hip joint, including the steps of: making a superiorly positioned incision; and preparing the femoral canal of a patient's natural femur for receipt of a femoral implant, through the superior incision, while the patient's natural femoral head is still within the patient's natural acetabulum.

These and other objects of the invention are also achieved by a tissue preserving hip surgical procedure for the replacement of a hip joint, including the steps of: preserving the short rotators and posterior capsule; and preserving the abductors.

DETAILED DESCRIPTION OF THE DRAWINGS

With reference to the drawings, a minimally invasive and tissue preserving hip replacement surgical procedure that meets and achieves all the objects of the invention set forth above will now be described.

Figure 1:
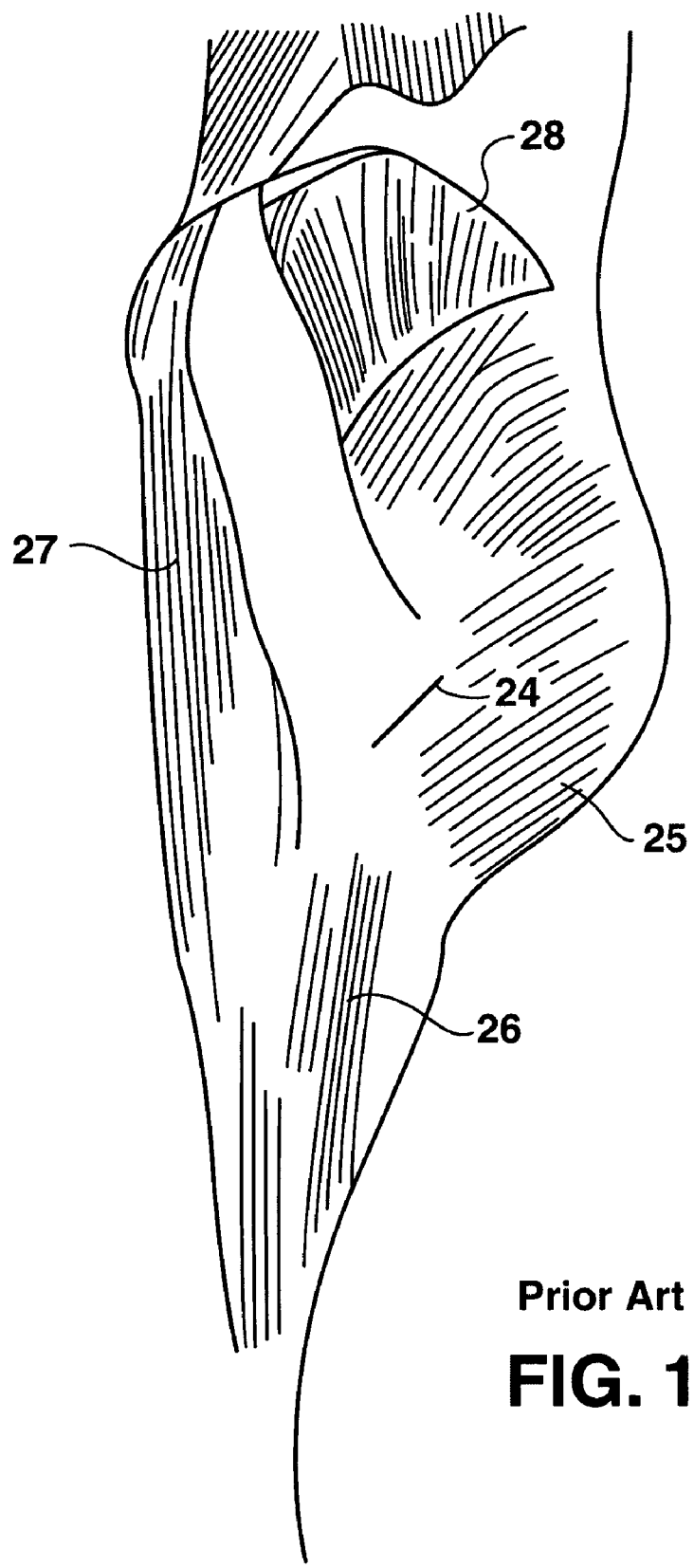
FIG. 1 is a depiction of the incision location of a prior art MIS hip procedure that uses a posterior approach.
Figure 2:
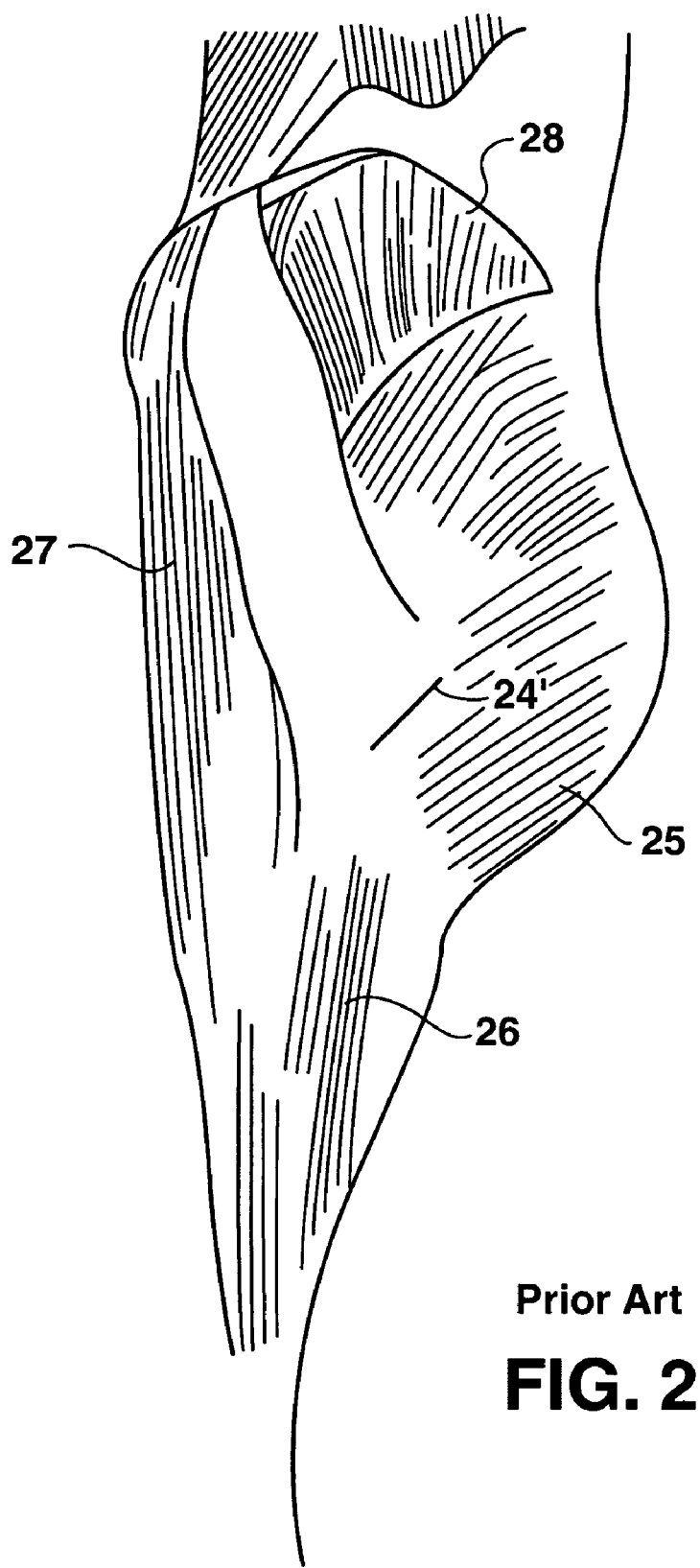
FIG. 2 is a depiction of the incision location of a variation of the prior art MIS hip procedure of FIG. 1 that uses a posterior approach.

FIG. 1 is a depiction of the incision location of a prior art MIS hip procedure that uses a posterior incision 24. FIG. 2 is a variation of FIG. 1 with incision 24'. FIGS. 1 and 2 show the main muscle groups around the hip joint which are the gluteus maximus 25, the ilio-tibial tract 26, the tensor fascia late 27 and the gluteus medius 28. The surgical method related to this posterior approach is disclosed in WO03/065906, which is incorporated by reference herein.

To prepare the hip for the total hip arthroplasty, the quadratus femoris (i.e., short external rotator) is released (i.e., dissected) from its femoral insertion. This will expose the posterior capsule of the hip joint. A thorough superior, posterior and inferior capsulotomy of the hip is performed and the hip dislocated. With forceful internal rotation of the hip, it is possible to carry out anterior capsulotomy of the joint.

Figure 3A:
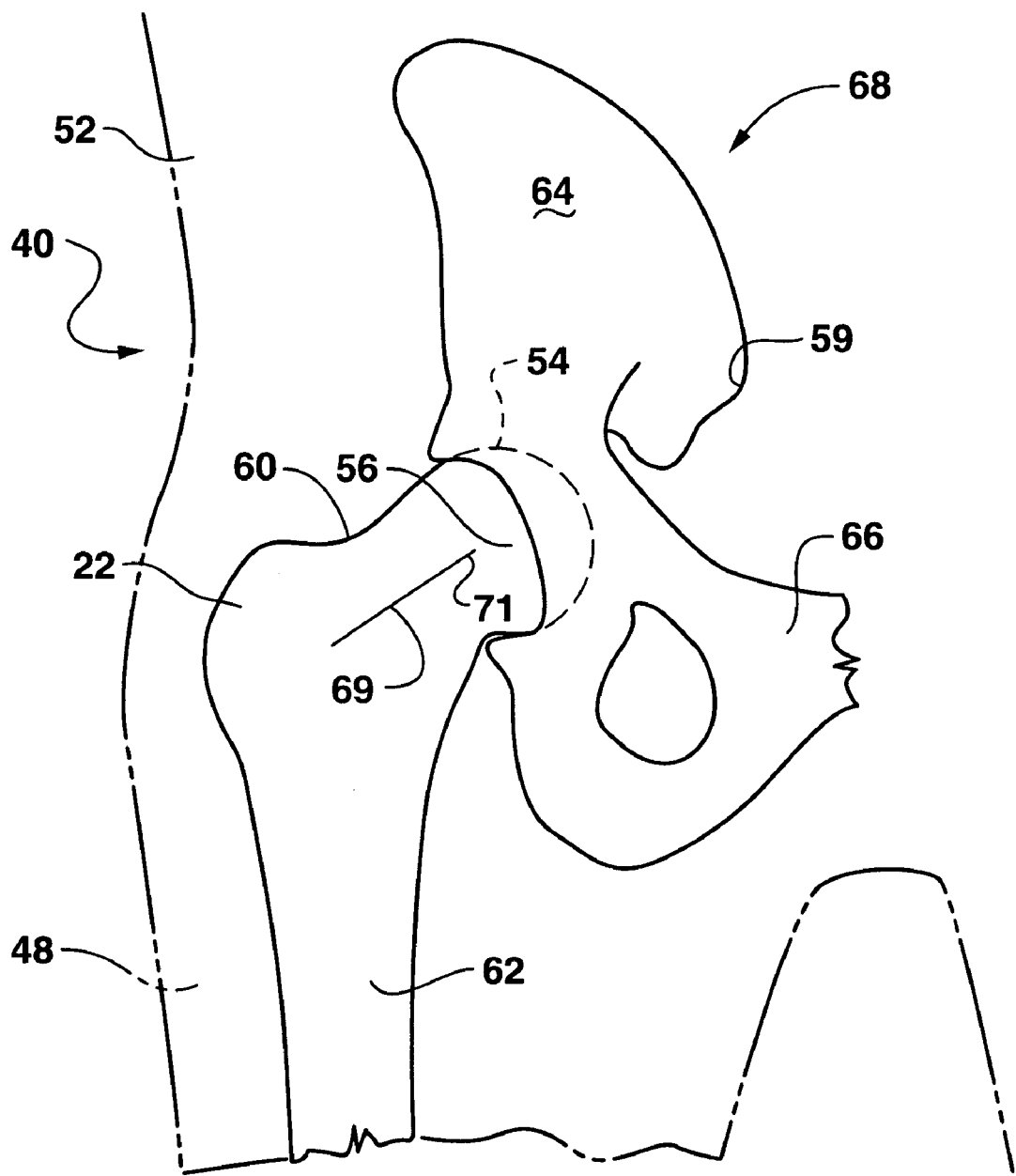
FIGS. 3A and 3B are depictions of the incision location of a prior art MIS hip procedure that uses posterior and anterior incisions and approaches.

FIG. 3A is a depiction of the incision location of another prior art MIS hip procedure; one that uses a combined anterior and posterior approach. According to the anterior approach, and as described in EP 1149562, which is incorporated herein, patient 40 is initially placed in a supine position (lying on their back) on a conventional operating table. Then, with leg 48 in a neutral position, two prominent bony landmarks are palpated, the anterior superior iliac spine (ASIS) 59 and the greater trochanter 22 of femur 62. Ilium 64 and pubis 66 of hip 68 are shown to better illustrate the relevant area of the body. The approximate anterior incision starting point 71 is identified two fingerbreadths inferior and two fingerbreadths anterior to the tuberical of the greater trochanter 22. The approximate finish point for the anterior incision is identified three fingerbreadths inferior and two fingerbreadths lateral to the anterior superior iliac spine (ASIS) 59. With the use of a spinal needle, the appropriate starting point 71 and the path of the anterior incision are identified by impaling the skin down to bone to confirm the central axis 69 of femoral neck 60.

Figure 3B:
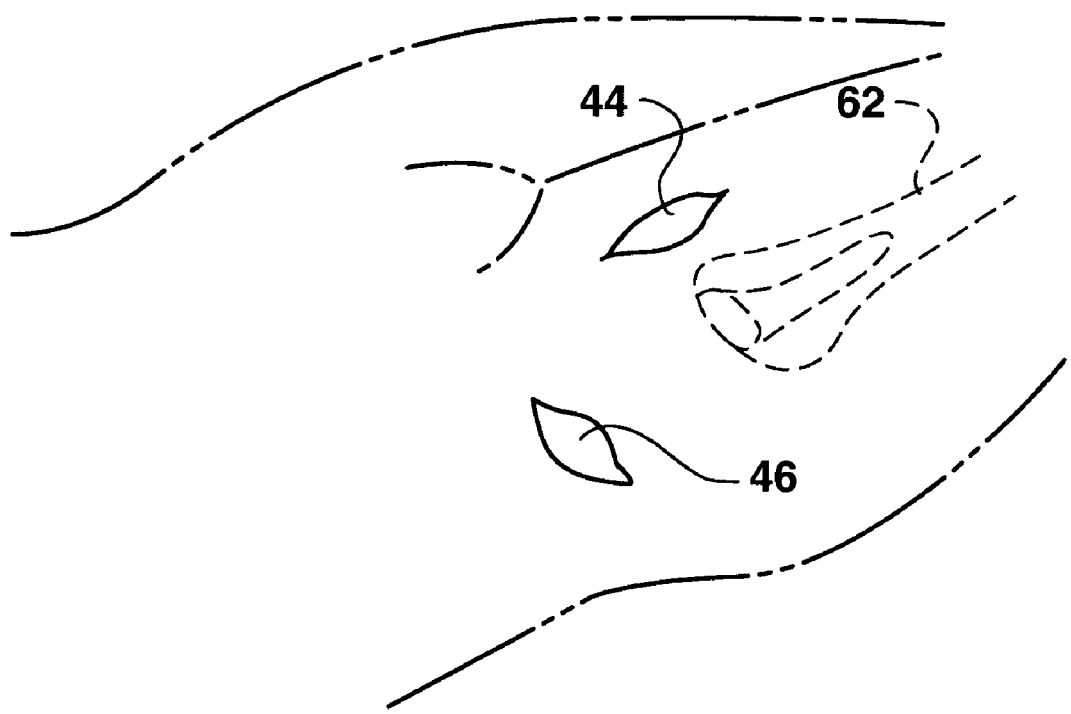

However, with this approach, a second—posterior—incision 46 (FIG. 3B) is used for insertion of the femoral implant and often visibility of the femoral canal and joint capsule through this posterior second incision is difficult. In fact, the method describes using the anterior incision for visibility. Furthermore, as with any posterior incision, since the gluteus medius and minimus are not well visualized and protected, they can be severely and permanently injured using this technique.

Based upon my review of, and experience with, these MIS approaches, I have concluded that there is a way to perform MIS hip surgery that is also tissue preserving.

In particular, concerning posterior incisions and approaches, I have found that post-operative healing related to posterior incisions is not always optimal as the short external rotators and posterior capsule are not at full strength initially and may never regain their anatomical integrity. Furthermore, post-operative dislocation rates increase with posterior incisions. Accordingly, it would be preferable to have a surgical method that does not implicate a posterior approach or incision.

Because much goes on in a very limited anatomical space during a hip MIS, it would also be preferable if the new surgical procedure had excellent hip capsule visualization and accessibility.

While incision location and approach are two ways to get a good visualization, another way is through how the incision and the fascia lata are kept open. It would be preferable if the new surgical method easily worked with ordinary retractors to keep the incision and fascia lata wide open while preventing surrounding soft tissue from being accidentally injured.

Finally, while this method is labeled as MIS because its incision size is typically less than 8 cm, what is actually more important to this invention is a surgical procedure in which the soft tissue, such as the posterior capsule, short external rotators, gluteus medius, and gluteus minimus are left in tact (e.g., not dissected or transected) whenever possible. Accordingly, the focus on the current procedure should be on the fact that it is tissue preserving and minimally invasive, whereas other procedures are merely minimally invasive.

Figure 4A:
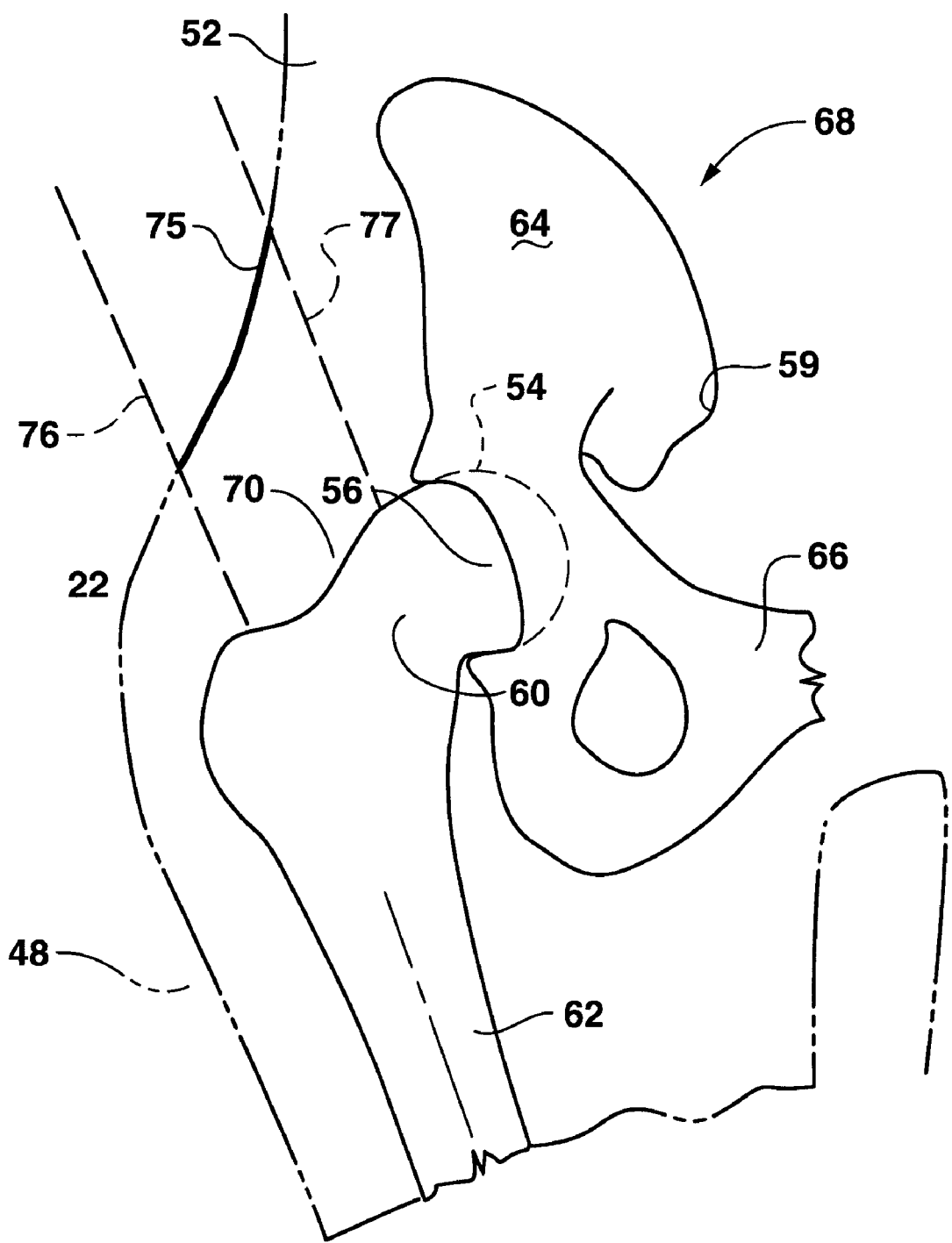
FIG. 4A is a depiction, similar to those above, showing the incision location of the MIS hip procedure according to the invention.

FIG. 4A is a depiction, similar to those discussed above, showing the incision location of the MIS hip procedure according to the invention. The incision 75 begins at a point 74, which is a projection of the tip of the greater trochanter 22 and proceeds superiorly about 8 cm. The location of the greater trochanter 22 can be identified by any known means, such as by palpation of leg 48.

It should be noted that during the MIS procedure according to the invention, the patient will typically be on his side, opposite to the side being operated on. Accordingly, incision 75 will be generally parallel to the operating room table (not shown) and the resulting opening will give a clear overhead view of the hip socket. Lines 76, 77 give a general indication of how a projection of the incision 75 boundaries give almost a complete overhead access to the greater trochanteric fossa 70. Furthermore, the patient's leg should be rotated (adducted) about 15 degrees inward.

Figure 4B:
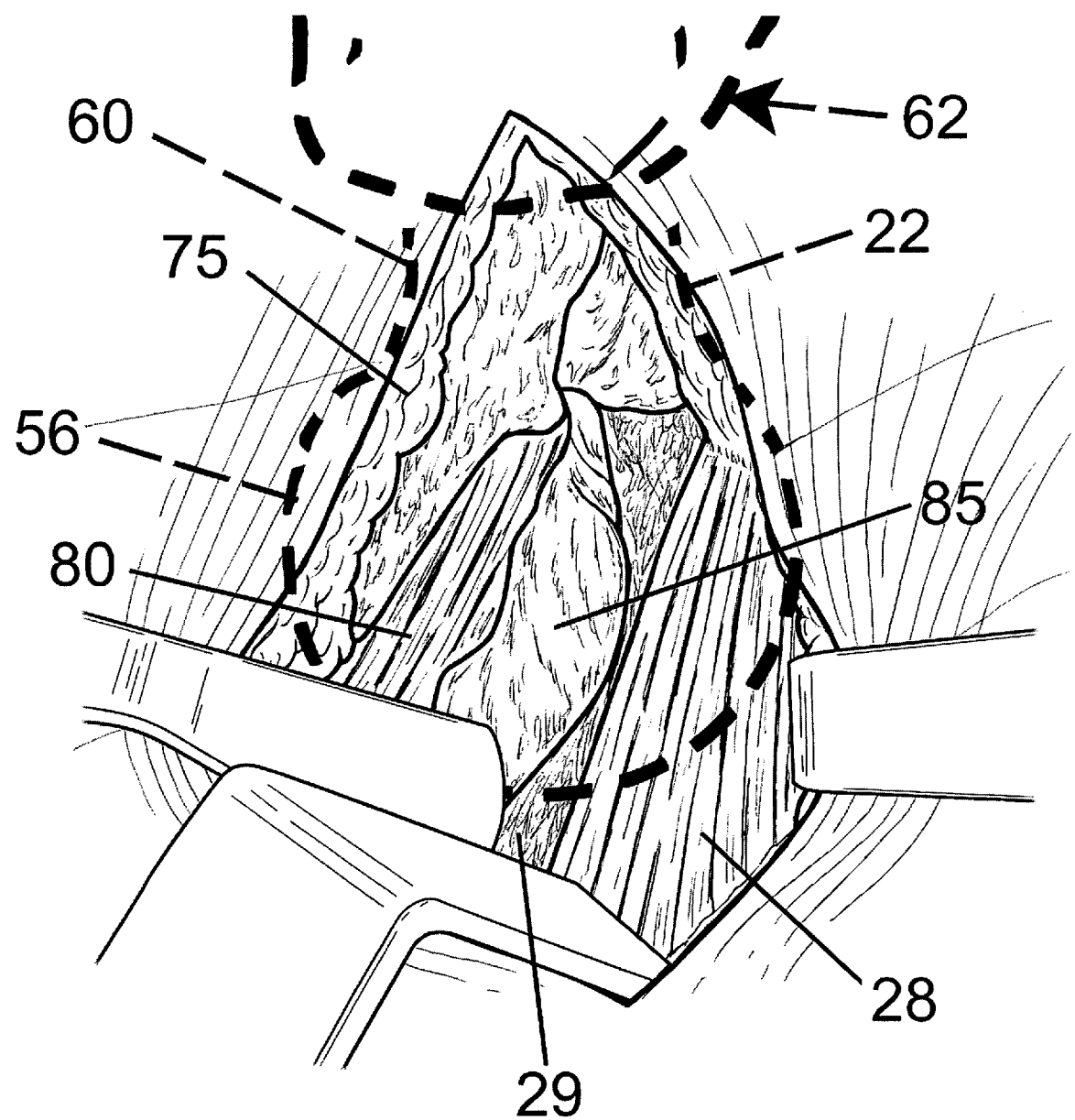
FIG. 4B depicts a detailed view of the incision area for the MIS hip procedure according to the invention.

FIG. 4B shows an intra-operative view of the incision site in preparation for the capsulotomy. Femur 62 is shown in projection under the soft tissue and showing the relative locations of the greater trochanter 22, femoral neck 60, and femoral head 56 relative to the incision 75. Furthermore, FIG. 4B shows how piriformis 80, gluteus minimus 29, and gluteus medius 28 are retracted to begin exposing the hip joint capsule 85, while protecting the aforementioned soft tissue from injury.

Thus, this overhead view and access to the hip joint will allow for a superior (vertical) capsulotomy to be performed on the hip joint.

Figure 5:
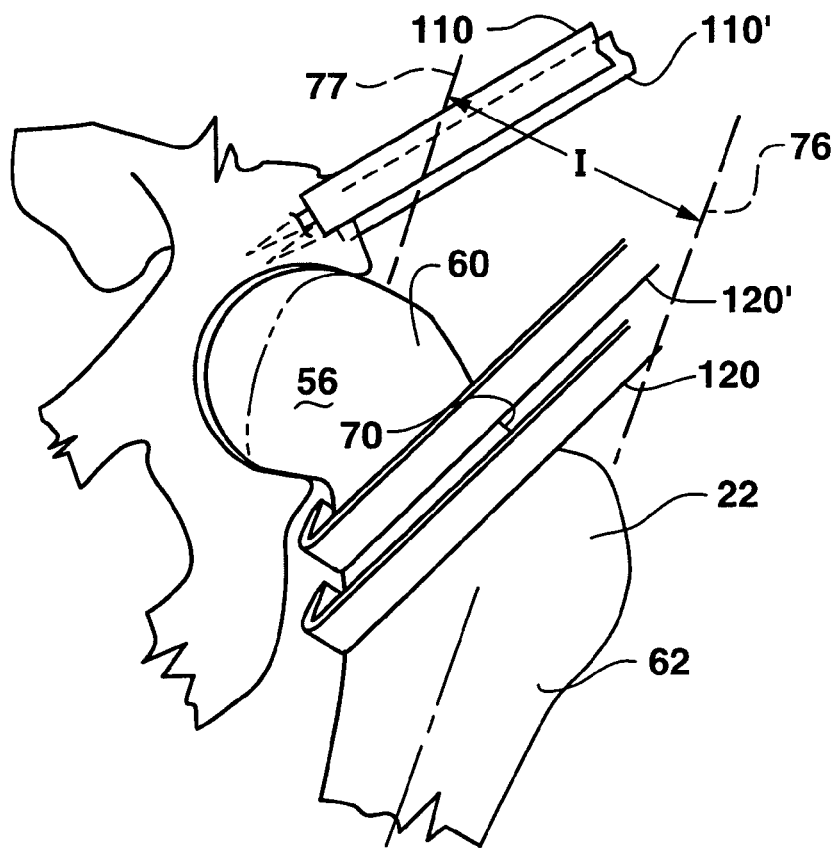
FIG. 5 depicts the use of retractors around the femoral neck in the MIS hip procedure according to the invention.

After the capsulotomy is performed, the retractors are released and then repositioned in the open hip capsule. FIG. 5 depicts how various retractors are used to keep the incision open a width I. First, a pair of leverage retractors 120, 120' can be inserted around the still intact femoral neck 60 to deflect the lower incision boundary 76 to prevent unwanted soft tissue from entering the surgical area. Though other MIS methods have alluded to the idea of not dislocating the hip during femoral canal preparation, those other methods have not taken the next step of using the femoral neck as a support for leverage retractors. Using the restrained femoral neck in this way and in combination with leverage retractors allows the incision to be kept wider open and provide better visibility without the need to dissect additional tissue; reinforcing the tissue preserving goal of the method. To keep the upper end of the incision open spiked Homan retractors 110, 110' can be driven into the ilium and used to deflect the tissue surrounding the upper end of the incision boundary 77.

Though these various retractors 110, 110', 120, 120' are not shown in all the following figures for clarity's sake, of course the incision 75 is retracted open its width I by such retractors.

Figure 6:
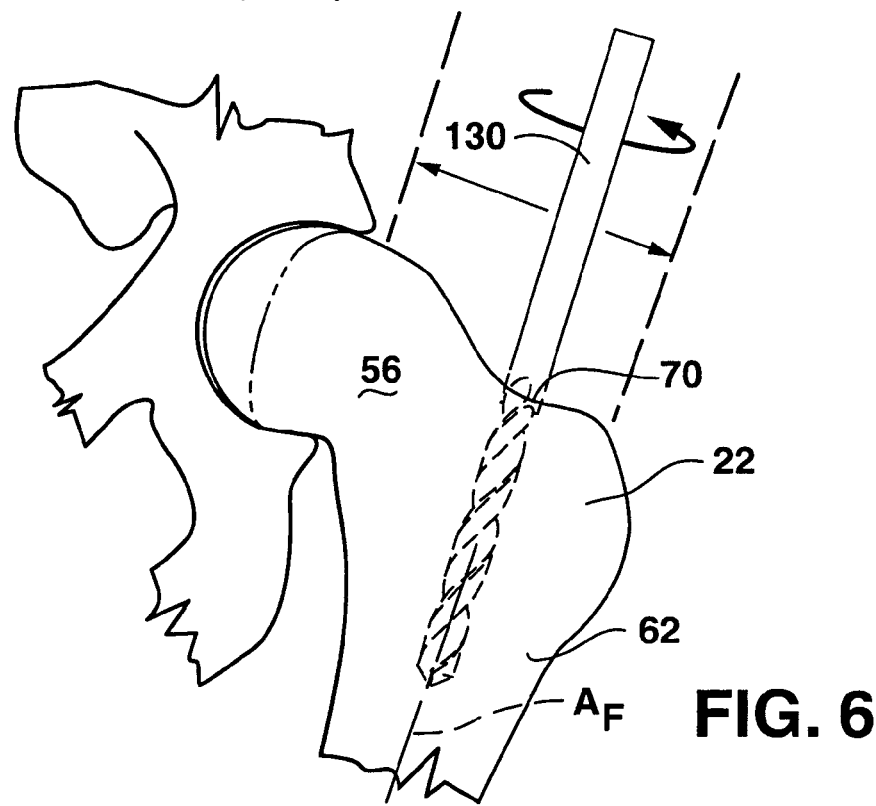
FIG. 6 depicts the drilling of the greater trochanteric fossa in the MIS hip procedure according to the invention.

FIG. 6 depicts how, with this superior incision, the femoral drill and bit 130 can be inserted directly in-line with the femoral axis AF. The superior incision also provides for excellent visibility of the greater trochanteric fossa 70 and a straight insertion of the drill bit. As is known in the art, sequential drilling, with progressively increasing diameter drill bits, is carried out until the femoral canal is drilled out enough to receive the femoral broach.

Figure 7:
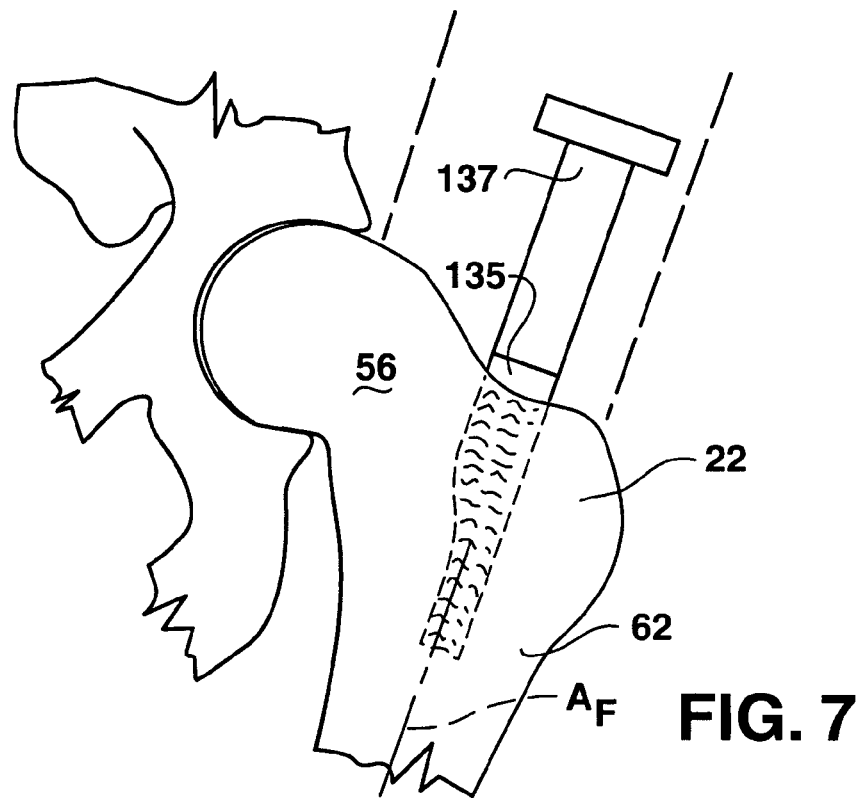
FIG. 7 depicts the broaching of the femoral canal in the MIS hip procedure according to the invention.

FIG. 7 depicts how with this superior incision, the femoral broach 135 held on its handle 137 can be inserted and operated (i.e., impacted) directly in-line with the femoral axis. As with femoral drilling and as known in the art, sequential broaching, with progressively increasing broach sizes, is carried out until the femoral canal is ready to receive the femoral trial. However, as shown in FIG. 8, the final broach is left in the prepared femoral canal for the moment and used for templating during the final resection of the femoral neck as will be described below.

Figure 8:
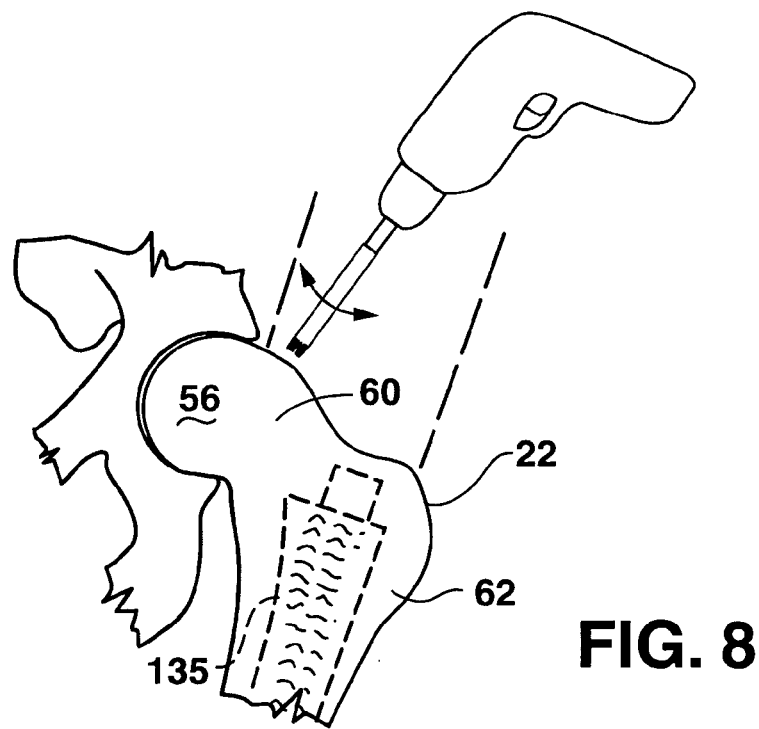
FIG. 8 depicts the resecting of the femoral head in the MIS hip procedure according to the invention.
Figure 9A:
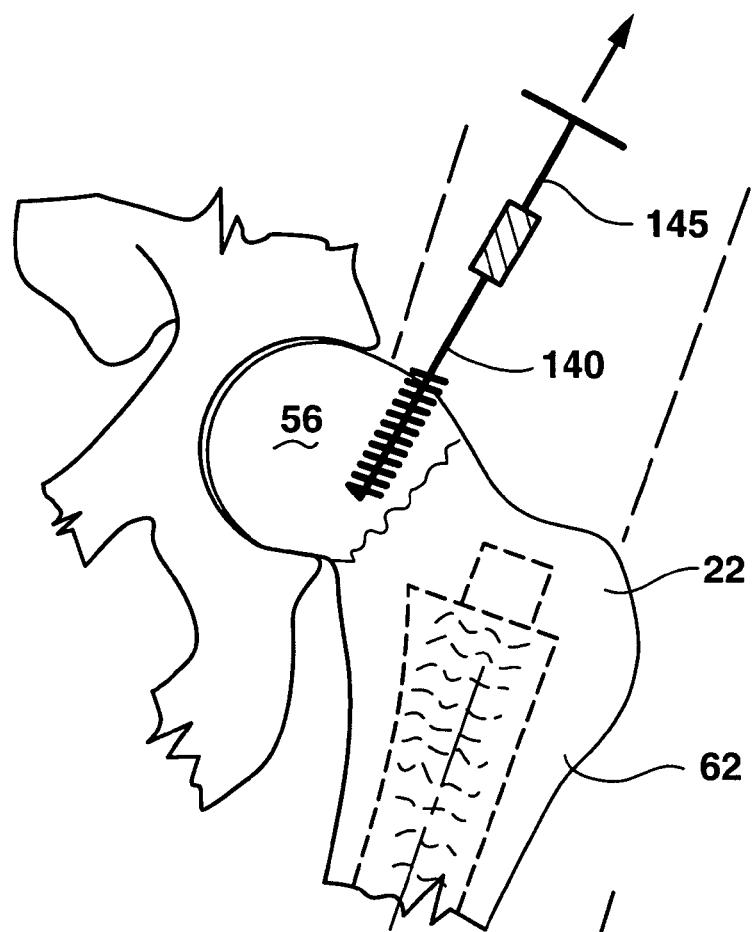
FIG. 9A depicts the removal of the femoral head from the acetabulum in the MIS hip procedure according to the invention.
Figure 9B:
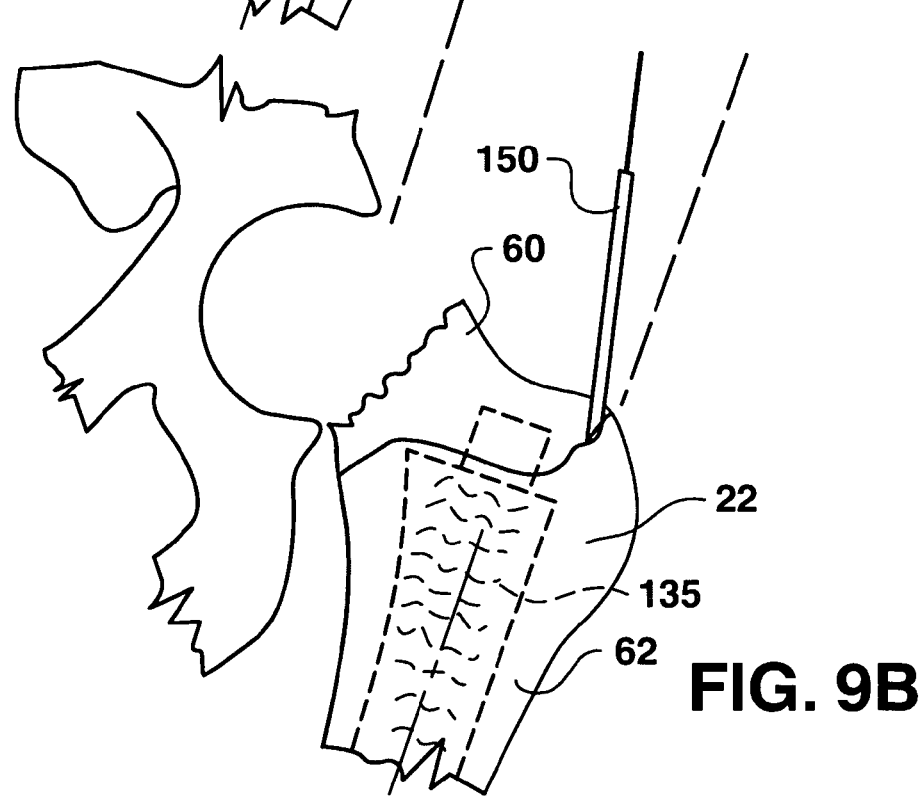
FIG. 9B depicts the resecting down of the remainder of the femoral neck in the MIS hip procedure according to the invention.

As shown in FIG. 8, a conventional oscillating saw is then used to resect the femoral head 56 from the femoral neck 60. As shown in FIG. 9A, after a screw 140 is drilled into the resected femoral head 56, the head 56 can be removed from the acetabulum using a T-chuck 145.

As shown in FIG. 9A, after the remainder of the femoral neck 60 is removed using osteotome 150 and the femoral broach 135 as a template. With the femoral broach 135 countersunk into the femur, the surgeon can clearly visualize the necessary fracture line to bring down the remainder of the femoral neck 60.

Figure 10:
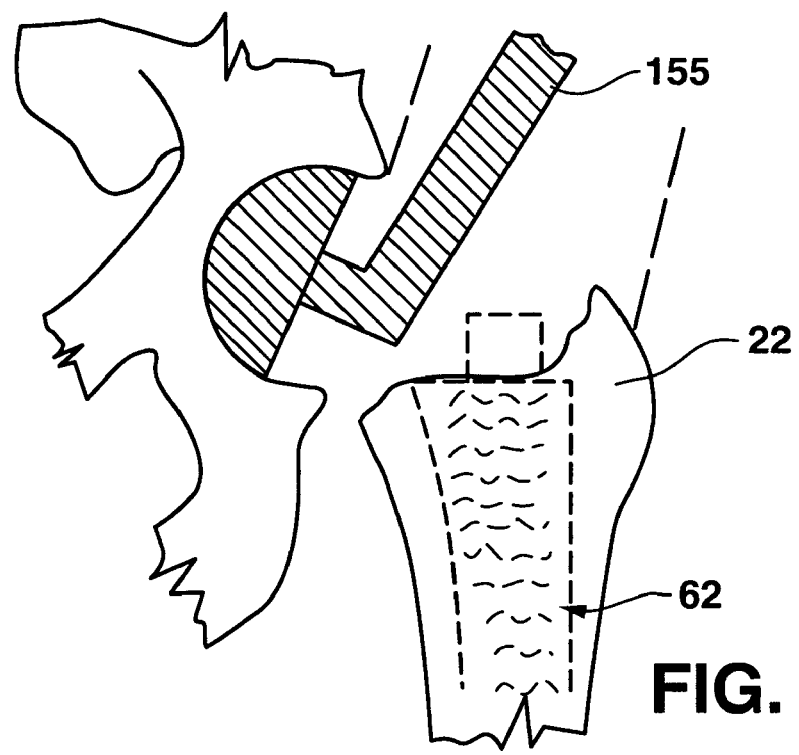
FIG. 10 depicts the reaming of the acetabulum in the MIS hip procedure according to the invention.

As shown in FIG. 10, the acetabulum is reamed to the proper size. A 45 degree angled reamer 155, such as shown in WO03/057049 (Waldemar Link), and incorporated by reference herein, has been shown to fit very well in this limited space.

Figure 11:
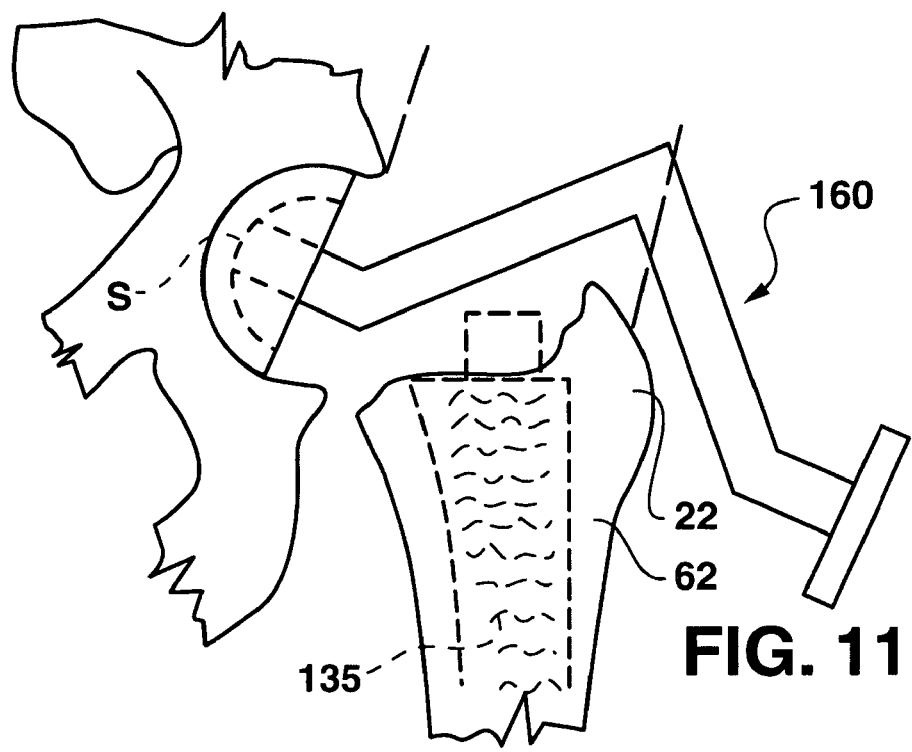
FIG. 11 depicts impaction of the acetabular shell in the MIS hip procedure according to the invention.
Figure 12:
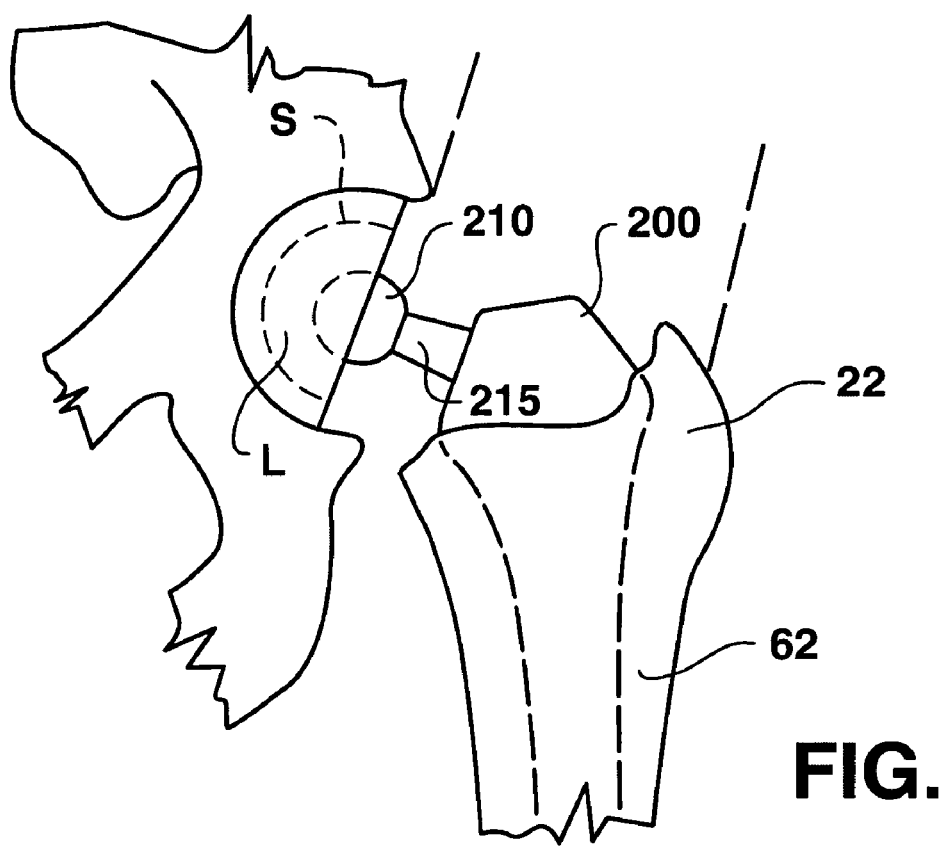
FIG. 12 depicts the trial reduction in the MIS hip procedure according to the invention.

As shown in FIG. 11, the acetabular shell S is then impacted into place using an acetabular impactor 160. An impactor 160 especially suitable for this purpose is described in assignee's co-pending application serial number. At this point, i.e., during impaction of the acetabular shell S, computer assisted navigation or an alignment frame may be used by the surgeon to assist him in setting varus and valgus, as described in our co-pending application. The shell liner L is then positioned. Additionally, if the acetabular shell is to be retained in the ilium with screws, the screws can be implanted via any suitable method, including through a percutaneous second incision distal and anterior to the vastus tubercle of the greater trochanter.

The femoral broach 135 is then removed from the femoral canal and replaced with the trial femoral stem 200. The trial femoral head 210 is inserted on the neck 215 of the trial femoral stem 200 and the hip palpated to allow the trial femoral head 210 to move into its position within the acetabular liner L. Leg length and range of motion is verified.

The hip joint is then, for the first time, dislocated. However, because the trial femoral head 210 is typically substantially smaller than the natural femoral head, dislocation at this point is not as disruptive to the surrounding soft tissue and the hip joint, itself, as would be a dislocation of the natural hip.

Once the hip joint is dislocated, if leg length and range of motion are acceptable, the trial femoral head 210 and stem 200 are removed and the final femoral implant and head inserted through the superior incision and in a conventional manner according to the instructions accompanying the implant. If leg length and range of motion are not acceptable, the surgeon may further prepare the hip joint and then re-check.

Generally, this method has been described with reference to a total hip joint replacement. However, this method can be just as easily used in a partial hip joint replacement, where only of either the acetabulum or femoral head are replaced by an implant. Therefore, when replacement of the "hip joint" is referred to, what is meant is either of the femoral or acetabular sides of the hip joint.

The tissue preserving and minimally invasive hip replacement surgical procedure has been described with respect to a preferred method for carrying out the procedure. However, the procedure is not limited to that method and when determining whether variations fall within the scope of the invention, reference should be made to the appended claims.

That which is claimed:

1. A tissue preserving surgical procedure for the replacement of a hip joint, including a step consisting of making a single incision for accessing the hip joint, said incision being a superior incision, wherein the superior incision begins at a point which is a superior projection of a tip of a greater trochanter and the superior incision proceeds superiorly for about 8 cm or less, making a superior capsulotomy for accessing the hip joint, the superior capsulotomy being carried out through the superior incision, and wherein said superior capsulotomy is performed while preserving most or all of the short rotators and the posterior capsule.

2. The surgical procedure according to claim 1, wherein said superior capsulotomy is performed while preserving all of the short rotators and the posterior capsule.

3. A minimally invasive and tissue preserving surgical procedure for the replacement of a hip joint, including the steps of:

making a superiorly positioned incision; and preparing the femoral canal of a patient's natural femur for receipt of a femoral implant, through said superior incision, while the patient's natural femoral head is still within the patient's natural acetabulum.

4. The procedure of claim 3, wherein said step of preparing said femoral canal is carried out without the need to transect any of the patient's abductors.

5. The procedure of claim 3, wherein said step of preparing said femoral canal is carried out without dissecting any of the patient's abductors.

6. The procedure of claim 5, wherein said step of preparing includes leaving the femoral broach in the femur for use as a template.

7. The method of claim 5, further comprising performing a vertical capsulotomy on the hip joint and placing retractors inside the hip joint on both sides of the femoral neck while said femoral head is within the acetabulum.

8. The method of claim 6, further comprising the step of extracting the patient's natural femoral head from the patient's natural acetabulum, after said step of preparing the femoral canal.

9. The procedure of claim 8, wherein said step of extracting includes simultaneously severing the patient's natural femoral head from the patient's femur.

10. The procedure of claim 9, further including the step of preparing the patient's natural acetabulum for receipt of an acetabular shell, through said superiorly positioned incision.

11. The procedure of claim 10, wherein said step of preparing the patient's natural acetabulum is carried out using an angled reamer.

12. The procedure of claim 11, wherein said angled reamer is hand-held.

13. The procedure of 12, further comprising the step of inserting an acetabular shell and liner in said prepared natural acetabulum through said superior incision.

14. The procedure of claim 13, wherein said femoral implant is inserted in said femoral canal through said superior incision after the insertion of said acetabular shell and liner.

15. The procedure of claim 14, wherein a femoral ball implant is implanted in the patient after the insertion of the femoral implant and the acetabular shell and liner.

16. The procedure of claim 3, wherein said step of preparing said femoral canal is carried out while preserving the short rotators and posterior capsule; and preserving the abductors.

17. The surgical procedure according to claim 3, further comprising making a superior capsulotomy for accessing the hip joint, the superior capsulotomy being carried out through the superior incision.

18. The surgical procedure according to claim 17, wherein said superior capsulotomy is performed while preserving most or all the short rotators and the posterior capsule.

* * * * *